United States Patent [19]

Evans

[11] Patent Number: 4,798,825

[45] Date of Patent: Jan. 17, 1989

[54] PYRETHRUM STABILIZATION BY INACTIVATION OF NATURAL ACETYLENIC IMPURITIES

[75] Inventor: April J. Evans, Glen Ellyn, Ill.

[73] Assignee: Amoco Corporation, Chicago, Ill.

[21] Appl. No.: 98,849

[22] Filed: Sep. 21, 1987

Related U.S. Application Data

[63] Continuation of Ser. No. 639,118, Aug. 9, 1984, abandoned.

[51] Int. Cl.$^4$ ............................................. A01N 65/00
[52] U.S. Cl. ...................................................... 514/65
[58] Field of Search ............................................ 514/65

[56] References Cited

U.S. PATENT DOCUMENTS 2,375,773  5/1945  De Jonge .......................... 424/186

FOREIGN PATENT DOCUMENTS 857541  12/1960  United Kingdom ................ 560/124
1332962  10/1973  United Kingdom ................ 560/124

*Primary Examiner*—Leonard Schenkman
*Assistant Examiner*—Joseph A. Lipovsky
*Attorney, Agent, or Firm*—Anthony J. Janiuk; William H. Magidson; Ralph C. Medhurst

[57] ABSTRACT

A composition and method for obtaining an improved stable composition of naturally occurring pyrethroid substances which naturally contain polyacetylenic substances includes inactivating the polyacetylenic substances by selective hydrogenation or removal of the polyacetylenic substances by extraction.

12 Claims, No Drawings

PYRETHRUM STABILIZATION BY INACTIVATION OF NATURAL ACETYLENIC IMPURITIES

This is a continuation of application Ser. No. 639,118, filed Aug. 9, 1984, now abandoned.

BACKGROUND OF THE INVENTION

This invention relates to improved compositions of natural pyrethroid insecticidal substances and a method for preparing such compositions. More particularly, this invention relates to a composition including a mixture of naturally occurring pyrethroid substances containing naturally occurring polyacetylenic substances in which the polyacetylenic substances are inactivated or removed.

Pyrethrum is a naturally occurring mixture of insecticidal substances obtained from the flowers of the tropical chrysanthemum, including *Chrysanthemum cinerariifolium*, *Chrysanthemum coccineum*, or *Chrysanthemum marshallii*. There are six active substances in naturally occurring pyrethrum: pyrethrin I and II, jasmolin I and II and cinerin I and II. The substances have the following structure:

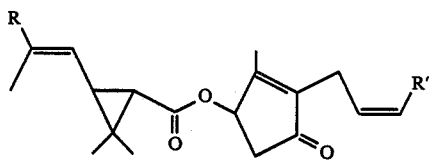

wherein R' is CH=CH$_2$ (pyrethrin), CH$_2$CH$_3$ (jasmolin), or CH$_3$ (cinerin) and R is CH$_3$ (I) or CO$_2$CH$_3$ (II). Pyrethrin I is most active for kill and pyrethrin II is most active for knockdown.

Pyrethrum possesses unusually fast contact insecticide action causing paralysis in a few moments and yet has little mammalian toxicity. Pyrethrum, one of the first widely used insecticides, remains commercially important today. Use of pyrethrum grew steadily until World War II when DDT, an inexpensive insecticide, became readily available. Current concern over the environmental acceptability of synthetic insecticides has renewed interest in pyrethrum.

The poor stability of pyrethrum, which breaks down rapidly upon exposure to oxidating compounds and light, may have less long term environmental impact than long acting substances such as DDT. However, its short active time has seriously limited its large scale use in agriculture. In order to maintain insecticide activity, frequent reapplication of pyrethrum is often necessary.

Although purified pyrethrum compositions are quite stable in dilute solution, decomposition increases rapidly with increasing concentration. Concentrated thin films that remain on plant or soil surfaces after application of the insecticides are largely decomposed after one day. It is well known that ultraviolet light causes extensive decomposition, and naturally occurring oxygen is also thought to be damaging. In the past, pyrethum compositions have been stabilized by the addition of traditional stabilizers, ultraviolet light absorbing substances, and anti-oxidants which have improved stability but have not totally eliminated decomposition.

One would expect that naturally occurring polyacetylene compositions, which strongly absorb ultraviolet light, would contribute to the overall stability of pyrethrum. Polyacetylenic compounds are compounds which contain more than one carbon-carbon triple bond. We have found, surprisingly, that naturally occurring polyacetylenes accelerate pyrethrum decomposition. Most chrysanthemums contain polyacetylenes which can contribute to pyrethrin decomposition.

Manufacturers extract and concentrate the active substances of pyrethrum from natural plant sources in extracts containing about 20% pyrethrins. Unfortunately, polyacetylenic substances are concentrated and removed from the plant residue along with the pyrethroid substances. There are two classes of naturally occurring polyacetylenes which contribute to the decomposition of pyrethrum. The two classes of polyacetylene substances are of the general formulae:

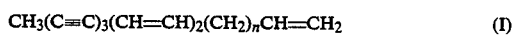  (I)

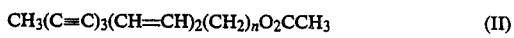  (II)

wherein n=2 or 3. Hereinafter, when referring to one or the other class of polyacetylene substances the terms polyacetylene I or polyacetylene II will be used.

SUMMARY OF THE INVENTION

One object of this invention, therefore, is to provide a method for producing stable concentrated pyrethroid compositions extracted from natural sources.

The object of the present invention can be obtained by reducing the concentration of naturally occurring acetylenic compounds in pyrethroid compositions. One embodiment of the present invention would include a method wherein after prompt extraction of dried flowers, the extract containing a mixture of pyrethroid substances and polyacetylenic substances is treated to inactivate or remove polyacetylene substances to minimize pyrethrum loss and retard subsequent decomposition.

A still further embodiment of the present invention includes a composition comprising a mixture of naturally occurring pyrethroid substances and naturally occurring polyacetylenic substances wherein said polyacetylenic substances are deactivated or removed.

The polyacetylenes may be inactivated using selective chemical reactions. Any selective chemical reaction that would modify the polyacetylene without affecting pyrethrin functionality would be suitable. A preferred reaction would be hydrogenation of the extract using a Lindlar catalyst. Lindlar catalyst comprises palladium, calcium carbonate and lead oxide and is highly effective for the selective hydrogenation of triple bonds to cis double bonds. Hydrogenation is performed in the presence of hydrogen at a slight positive pressure with agitation. See L. F. Fieser and M. Fieser, *Reagents for Organic Synthesis*, John Wiley & Son, New York, N.Y., p. 566 (1967) which is incorporated by reference herein. The Lindlar catalyst, or other selective hydrogenation catalysts, can be used to reduce triple bonds to double bonds. Inactivation of the naturally occurring polyacetylenes contributes to the stability of pyrethrum. The method results in a novel composition including a mixture of naturally occurring pyrethrum and inactivated polyacetylenic substances.

Class I polyacetylenic compounds are also subject to deactivation by removal through extraction processes. For example, a naturally occurring mixture of polyacetylene I substances and pyrethrum may be separated by extracting the pyrethrum with a polar solvent, such methanol or nitromethane. The polyacetylene I substances may be extracted with a saturated paraffin, such as pentane, hexane, or heptane, or another nonpolar solvent such as carbon tetrachloride. Polyacetylene II substances are solids at room temperature and can be crystallized out of a naturally occurring mixture including pyrethrum in a medium polarity solvent, such as diethel ether, acetone or toluene at temperatures below 25° C. and above the crystallization temperatures of the individual components of pyrethrum, such that the pyrethroid substances remain in solution.

Preferably, the stabilized composition of natural pyrethroid substances has a weight ratio of polyacetylenic compounds to pyrethrum of less than 1 to 10 or 1 to 20. Even more preferred are weight ratios of polyacetylenic compounds to pyrethrum of less than 1 to 100 (hereinafter all weights and weight ratios refer to weight on a dry weight basis). Any method or combination of methods for inactivation of polyacetylenic compounds in pyrethrum compositions can be utilized.

EXAMPLE

The present invention is illustrated in the following example which exemplifies certain features including preferred weight ratios.

Samples of pyrethrum I—containing pyrethrin I, jasmolin I and cinerin I—and samples of pyrethrum II—containing pyrethrin II, jasmolin II and cinerin II—were carefully purified by thin layer chromatography. Three samples of pyrethrum I, each weighing 95 micrograms, were placed in three vials. Similarly, three samples of pyrethrum II, each weighing 65 micrograms, were placed in three vials. Into one vial of each pyrethrum I and pyrethrum II group of vials, were added 7.4 micrograms of polyacetylene II. Into a second vial of each pyrethrum I and pyrethrum II group of vials, were added 74 micrograms of polyacetylenic II compounds. The third vial of each group was not altered. The contents of each vial were mixed well with a few drops of solvent, the solvent was evaporated, and the concentrated residue was stored in the dark under air for one week. After one week, one milliliter of acetonitrile was added to each sample and they were analyzed by high pressure liquid chromatography. Results are illustrated as set forth below:

TABLE I

Relative Amounts of Pyrethrum Remaining After One Week Storage

| Compound | Polyacetylene Concentration (%) | | |
|---|---|---|---|
| | 0 | 5 | 46 |
| Pyrethrin I | 100 | 45 | 0 |
| Jasmolin I | 8 | 7 | 3 |
| Cinerin I | 14 | 13 | 6 |
| Pyrethrin II | 66 | 33 | 3 |
| Jasmolin II | 7 | 8 | 4 |
| Cinerin II | 16 | 16 | 10 |

When an approximately equivalent amount (74 ug) of polyacetylenic II substances was present, significant decomposition of jasmolins and cinerins, both I and II, and nearly total decomposition of pyrethrins, both I and II, occurred. Little or no decomposition of cinerins and jasmolins, both I and II, but roughly 50% decomposition of pyrethrins, both I and II, was seen in the presence of 0.1 equivalent (7.4 ug) of polyacetylene II substances. The largest amounts of pyrethrum I and II remained in the samples with no added polyacetylene substances. These results show that naturally occurring polyacetylene substances accelerates the decomposition of all components of naturally occurring pyrethrum. The removal or deactivation of naturally occurring polyacetylenic compounds from naturally occurring pyrethrum will produce a more stable composition.

Pyrethroid substances which can be utilized in this invention include naturally occurring materials such as pyrethrum esters—the well-known pyrethrins I and II, cinerins I and II and the jasmolins I and II. The process can be utilized with extracts of whole plants or extracts from cell cultures.

The pyrethrum material processed in accordance with the present invention can be dispersed in a conventional and well-known manner in a suitable carrier for use as an insecticide having improved stability. Such carriers can include a dry powder, such as clay or talc, or an organic-based liquid adapted for spray or aerosol application, or for admixture with water to form an aqueous emulsion.

Additionally, stabilizers, enhancers and other agents utilized to enhance the activity of pyrethrum, which are well-known in the art, can also be added to the composition. Such stabilizers include anti-oxidants and ultraviolet stabilizers.

Thus, while preferred embodiments have been illustrated and described, it is understood that the present invention is capable of variation and modification and, therefore, should not be limited to the precise details set forth, but should include such changes and alterations as fall within the purview of the following claims.

I claim:

1. A composition comprising: a mixture of naturally occurring pyrethroid substances and derivatives of naturally occurring polyacetylenic substances wherein said derivatives of polyacetylenic substances are formed by substantially inactivating the acetylenic functional groups to promote the stability of the pyrethroid substances.

2. The composition of claim 1 wherein said polyacetylenic substances are selectively hydrogenated.

3. The composition of claim 1 wherein said polyacetylenic substances are selectively hydrogenated by a Lindlar catalyst reaction.

4. The composition of claim 1 wherein said polyacetylenic substances are selectively hydrogenated by a Lindlar catalyst in the presence of hydrogen at a slight positive pressure.

5. The composition of claim 1 wherein the weight ratio of naturally occurring polyacetylenic substances remaining active to pyrethroid substances is less than 1 to 10.

6. The composition of claim 1 wherein the weight ratio of naturally occurring polyacetylenic substances remaining active to pyrethroid substances is less than 1 to 100.

7. A method for producing a composition of natural pyrethroid substances from mixtures containing natural pyrethroid substances and natural polyacetylenic substances comprising: the step of substantially inactivating naturally occurring polyacetylenic substances to promote the stability of the pyrethroid substances.

8. The method of claim 7 wherein the weight ratio of polyacetylenic substances to pyrethroid substances is less than 1 to 10.

9. The method of claim 7 wherein the weight ratio of polyacetylenic substances to pyrethroid substances is less than 1 to 100.

10. The method of claim 7 wherein the concentration of active natural polyacetylenic substances is reduced by selective hydrogenation.

11. The method of claim 7 wherein the concentration of active natural polyacetylenic substances is reduced by selective hydrogenation by a Lindlar catalyst reaction.

12. The method of claim 7 wherein the concentration of active natural polyacetylenic substances is reduced by selective hydrogenation by a Lindlar catalyst reaction in the presences of hydrogen at a slight positive pressure.

* * * * *